United States Patent [19]

Ridgway

[11] 4,291,063

[45] Sep. 22, 1981

[54] TREATMENT OF PROTEINACEOUS MATERIALS WITH ANHYDROUS AMMONIA GAS

[75] Inventor: John A. Ridgway, LaPorte, Ind.

[73] Assignee: Standard Oil Company (Indiana), Chicago, Ill.

[21] Appl. No.: 183,206

[22] Filed: Sep. 2, 1980

Related U.S. Application Data

[63] Continuation of Ser. No. 68,592, Aug. 22, 1979.

[51] Int. Cl.$^3$ .......................... A23J 3/00; A23L 1/34
[52] U.S. Cl. ..................................... 426/319; 426/656
[58] Field of Search .............................. 426/319, 656; 260/112 R, 123.5

[56] References Cited

U.S. PATENT DOCUMENTS

| | | | |
|---|---|---|---|
| 2,789,906 | 4/1957 | Zick | 426/319 X |
| 3,442,661 | 5/1969 | Mitchell | 426/319 |
| 3,615,654 | 10/1971 | Ayukawa et al. | 426/656 |
| 3,819,610 | 6/1974 | Akin | 426/656 X |
| 3,947,605 | 3/1976 | Chao | 426/656 |

*Primary Examiner*—Robert A. Yoncoskie
*Attorney, Agent, or Firm*—Gregory E. Croft; William T. McClain; William H. Magidson

[57] ABSTRACT

Proteinaceous materials such as yeast and soy flour can be treated with anhydrous ammonia gas at conditions sufficient to cause exothermic absorption of the ammonia to achieve improvements in certain properties such as texture and flavor.

9 Claims, No Drawings

TREATMENT OF PROTEINACEOUS MATERIALS WITH ANHYDROUS AMMONIA GAS

This is a continuation of application Ser. No. 68,592, filed Aug. 22, 1979.

BACKGROUND OF THE INVENTION

1. Field of the Invention

This invention relates to a method for improving the texture and/or flavor characteristics of certain proteinaceous materials such as yeasts or vegetable flours. More particularly it relates to a gaseous treatment with anhydrous ammonia vapor.

2. Description of the Prior Art

Flavor and texture improvement are two areas which receive continual attention in the food industry. In the case of soy flour, for example, a nagging problem facing users is the "beany" taste which limits the amounts of soy which can be incorporated into a food product without detracting from the product's flavor acceptability. Similarly, dried yeast also has a flavor problem, although to a lesser extent. In addition, dried yeast lacks sufficient textural strength to be used in certain foods in large quantities. Such yeast products typically disperse into single cells when contacted with water, and as such can impart a "mushy" texture to the product into which they are incorporated.

Flavor modification treatments for microorganisms have been developed using liquid solvents for flavor extraction. As an example, U.S. Pat. No. 3,615,654 (1971) to Ayukawa et al., teaches a liquid ammonia extraction of microbial cells at temperatures below the boiling point of liquid ammonia (−33.4° C.) for the purpose of improving flavor, color, odor, and taste of the microbial cell product, as well as reducing the ribonucleic acid content. After extraction the treated cells are separated from the liquid ammonia by conventional methods and recovered.

It has now been discovered that this solid-liquid separation step can be eliminated by the process of the invention, which utilizes a gaseous ammonia treatment. The gaseous ammonia treatment of this invention not only improves the flavor of proteinaceous materials, but also quite unexpectedly improves the texturization properties of yeasts.

SUMMARY OF THE INVENTION

This invention resides in a method of treating proteinaceous materials such as commercial spray-dried yeast, soy flour, or mixtures thereof by exposing the materials to gaseous anhydrous ammonia at conditions sufficient to cause an exothermic absorption of the ammonia by the proteinaceous material. Such conditions can preferably be achieved by subjecting the proteinaceous material to gaseous anhydrous ammonia at a pressure of from about 15 to about 45 percent of the vapor pressure of liquid ammonia at the treating temperature. Suitable temperatures are from about 0° C. to about 100° C. for a time sufficient to desirably alter the properties of the proteinaceous material. Generally, treatment times can be from about 15 minutes to about 2 hours, but are dependent on the results desired and the heat transfer capabilities of the apparatus being used. The particular reaction temperature used is dictated by the desired results, since increasing the reaction temperature causes an increase in the bitter flavor of the product, while at the same time increases the extractability of the nucleic acids. If a low degree of bitterness, rather than high nucleic acid removal, is the dominant consideration, then preferred temperatures are from about 0° C. to about 40° C., most preferably from about 20° C. to about 40° C., or at about room temperature.

When used for treating yeasts, this process improves the flavor, increases the water solubility of the nucleic acids present, and most importantly imparts texture to the yeast product by causing contraction and agglomeration of the yeast cells. The resulting agglomerates of shrunken yeast cells do not disperse when placed in water as do typical spray-dried yeast cells. *Candida utilis*, *Saccharomyces cerevisiae*, *Saccharomyces carlsbergensis*, and *Kluyveromyces fragilis* are preferred yeasts because of their current acceptance for food uses, although other yeasts will also benefit from this process.

When used for treating soy flour, this process improves the flavor by reducing the characteristic beany flavor.

EXAMPLES

The following examples will serve to illustrate various aspects of this invention without implied limitation.

Batchwise experiments were conducted to generally ascertain the effects of gaseous ammonia treatments. Although no attempt was made to optimize the process, those skilled in the art will appreciate that optimization can be readily achieved by routine experimentation. For each run the feed material was charged batch-wise and the system was placed under vacuum before being pressurized with ammonia. Agitation was continuously maintained during the steps of pressurizing, reacting, depressurizing, and evacuation in order to prevent excessive agglomeration and to promote heat transfer and avoid hot spots. Because of equipment limitations, the heat evolution made temperature control very difficult since the absorption of gaseous ammonia by spray-dried yeast is highly exothermic. (At a pressure of 125 psig an estimated 10–15% $NH_3$ is absorbed with heat evolution of 30–40 cal/gram of yeast. *Candida utilis* was the yeast selected for all the yeast experiments.) This heat evolution results in increasing the temperature of an adiabatic yeast sample from an initial 20° C. to a final level of 85°–90° C. However, the ammonia absorption is accompanied by physical and chemical changes in the treated material that manifest themselves in improved flavor, nucleic acid solubility, and texturability.

Reaction times were arbitrarily set at about one hour. During final evacuation the temperature was maintained at about 70° C. to remove residual ammonia. The time of evacuation varied depending on the degree of vacuum and residual ammonia tolerance.

In order to determine the solubles content, the treated products were subjected to a water extraction by dispersing the treated yeast in water at room temperature for 10 minutes and centrifuging to separate the solids and extract. The two fractions were recovered by evaporation and drying. The solubles content is reported as the "Extract Yield" in the table below and is defined as the weight percent of solubles recovered based on the weight of yeast charged to the extraction. The insoluble fraction was analyzed for nucleic acid content. (The initial nucleic acid content of the yeast was about 9 weight percent.) Representative experimental data is set forth in the following table.

| Feed | Treating | Ammonia |
| --- | --- | --- |

-continued

| Material | Temperature, °C. | Pressure, psig |
|---|---|---|
| Spray-dried yeast | Room Temp. | 0 |
| Spray-dried yeast | Room Temp. | 55 |
| Spray-dried yeast | Room Temp. | 115 |
| Spray-dried yeast | 30 | 0 |
| Spray-dried yeast | 42 | 90 |
| Spray-dried yeast | 90 | 125 |
| Soy flour | 25 | 100 |

| Extract Yield, % | Residual Nucleic Acid, % |
|---|---|
| 17.4 | 8.8 |
| 20.0 | 5.7 |
| 24.0 | 3.3 |
| 17.2 | 8.7 |
| 21.4 | 4.5 |
| 23.7 | 3.2 |

Flavor suffers increasingly from bitterness development as the contacting temperature is raised. At a treatment temperature of 0° C. the flavor of the treated material is excellent. However, at temperatures of 40° C. or greater a bitterness develops that is most apparent in the water-insoluble fraction of the product. The bitterness of the soluble fraction is not as severe. On the other hand, the nucleic acid solubility was found to increase as the NH₃ pressure and treating temperature were increased.

The texture of the treated product was improved in all cases. In the absence of agitation, the treated product can be recovered as a somewhat friable mass. With agitation, small agglomerates are formed and the individual cells become cemented together. The resulting agglomerates, or particles obtained by grinding the product made with no agitation, do not disperse when placed in water as does spray-dried yeast. As a result of this effect, the ammonia-treated spray-dried yeast does not impart a mushy texture to food products such as meat patties. A residual-ammonia content of 0.5–0.7% (by titration) is usually present in the treated product.

It will be apparent to those skilled in the art that many variations from these examples, shown for purposes of illustration, can be made without departing from the scope of this invention as defined by the following claims.

I claim:

1. A method for improving the texture of spray-dried yeast comprising exposing the spray-dried yeast to gaseous anhydrous ammonia at a treating temperature of from about 0° C. to about 100° C. and an ammonia pressure of from about 15 to about 45 percent of the vapor pressure of liquid ammonia at the treating temperature for from about 15 minutes to about 2 hours.

2. The method of claim 1 wherein the temperature is about room temperature.

3. The method of claim 2 wherein the yeast is *Candida utilis*.

4. The method of claim 1 wherein the temperature is from about 0° C. to about 40° C.

5. The method of claim 1 wherein the temperature is from about 20° C. to about 40° C.

6. The method of claim 1 wherein the yeast is *Candida utilis*.

7. The yeast product produced by the method of claim 1.

8. The yeast product produced by the method of claim 3.

9. The yeast product produced by the method of claim 6.

* * * * *